United States Patent [19]

Kampner

[11] Patent Number: 5,571,193
[45] Date of Patent: Nov. 5, 1996

[54] IMPLANT WITH REINFORCED RESORBABLE STEM

[76] Inventor: Stanley L. Kampner, 2320 Sutter St., San Fransisco, Calif. 94115

[21] Appl. No.: 897,197

[22] Filed: Jun. 11, 1992

Related U.S. Application Data

[63] Continuation-in-part of Ser. No. 850,091, Mar. 12, 1992, abandoned.

[51] Int. Cl.$^6$ ..................................................... A61F 2/30
[52] U.S. Cl. .................. 623/18; 623/16; 623/23
[58] Field of Search .................. 623/16, 17, 18, 623/19, 20, 21, 22, 23; 606/76, 77

[56] References Cited

U.S. PATENT DOCUMENTS

| | | |
|---|---|---|
| 2,112,007 | 3/1938 | Adams . |
| 3,463,158 | 8/1969 | Schmitt et al. . |
| 3,543,749 | 12/1970 | Grove . |
| 3,623,164 | 11/1971 | Bokros . |
| 3,787,900 | 1/1974 | McGee . |
| 3,840,904 | 10/1974 | Tronzo . |
| 3,899,556 | 8/1975 | Heide et al. . |
| 3,905,407 | 9/1975 | Long . |
| 3,929,971 | 12/1975 | Roy . |
| 4,120,730 | 10/1978 | Trojer et al. . |
| 4,192,021 | 3/1980 | Deibig et al. . |
| 4,195,366 | 4/1980 | Jarcho et al. . |
| 4,202,055 | 5/1980 | Reiner et al. . |
| 4,224,696 | 9/1978 | Murray et al. . |
| 4,344,190 | 8/1982 | Lee et al. . |
| 4,356,572 | 11/1982 | Guillemin et al. . |
| 4,484,570 | 11/1984 | Sutter et al. . |
| 4,488,391 | 12/1984 | von Recûm . |
| 4,495,664 | 1/1985 | Blanquaert . |
| 4,950,300 | 8/1990 | Langlais ..................... 623/16 |
| 4,990,161 | 1/1991 | Kampner . |
| 4,995,883 | 2/1991 | Demane et al. ............. 623/18 |
| 5,169,400 | 12/1992 | Muhling et al. ............ 606/77 |
| 5,197,990 | 3/1993 | Lawes et al. ............... 623/16 |

FOREIGN PATENT DOCUMENTS

| | | |
|---|---|---|
| 25 58 446 | 8/1976 | Germany . |
| 26 28 284 | 1/1977 | Germany . |
| 1026789 | 9/1972 | U.S.S.R. . |
| 4554 | 3/1881 | United Kingdom . |
| 2072514 | 2/1984 | United Kingdom . |
| WO90/09154 | 8/1990 | WIPO . |

*Primary Examiner*—Paul B. Prebilic
*Attorney, Agent, or Firm*—Townsend and Townsend and Crew

[57] ABSTRACT

A prosthetic implant for a bone joint has an anchor formed of a resorbable sleeve reinforced with a nonresorbable core. Also disclosed are methods of installation.

16 Claims, 4 Drawing Sheets

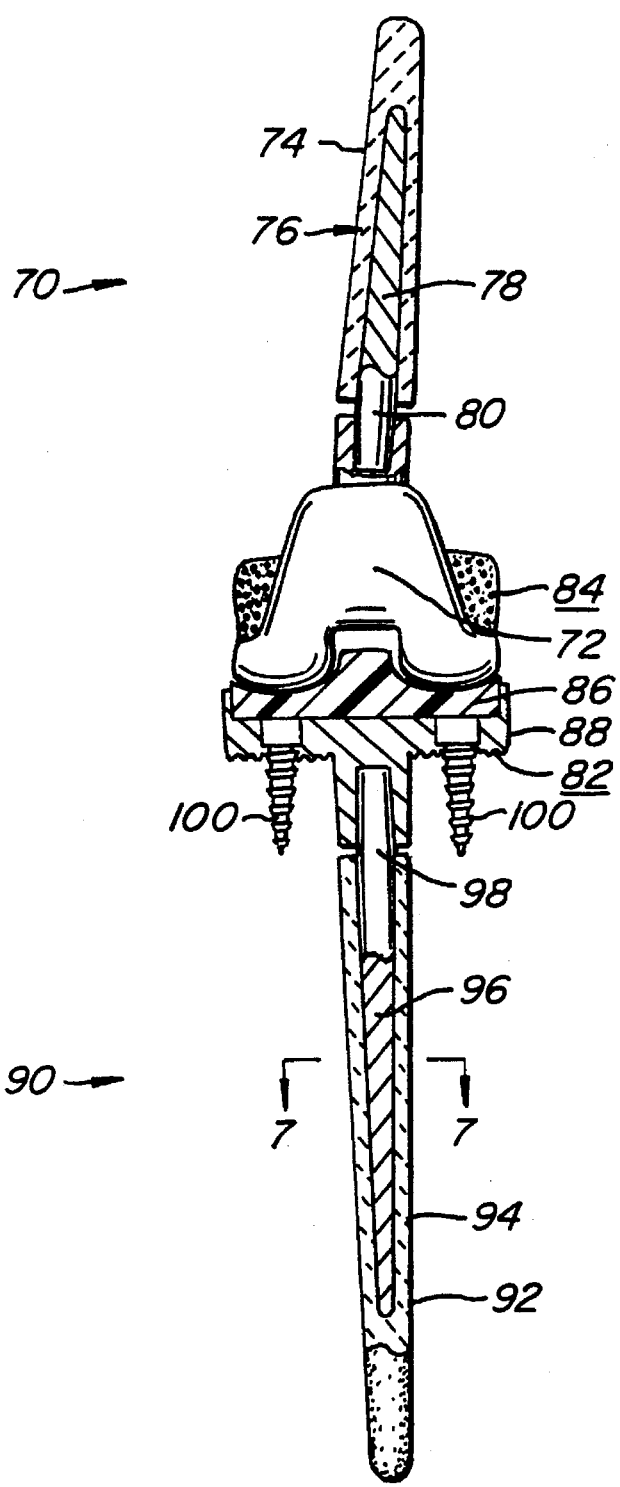
FIG. 7.
FIG. 4.

IMPLANT WITH REINFORCED RESORBABLE STEM

This application is a continuation-in-part of Ser. No. 07/850,891, filed Mar. 12, 1992, now abandoned.

BACKGROUND OF THE INVENTION

The prosthetic replacement of joints has evolved over the years from early, relatively crude models to current prostheses which closely replicate functions and motions of a natural joint. Some of the joints amenable to prosthetic replacement include the shoulder, hip, knee, ankle and wrist. Prosthetic joints have provided patients with increased comfort, range of motion and nearly normal lifestyles.

Some of the problems encountered with prosthetic joints include excessive wear between components of the prosthetic implants which move with respect to each other. Additionally, movement of the implant with respect to the patient's bone compromises fixation. A third problem is an abnormal stress transference from the implant to the bone.

To address some of the problems of fixing the implant to the bone, cemented implants have been developed. The cement initially acts as a grout to "form fit" the implant to the bone. After the cement cures to a hard material, it becomes mechanically fixed to the bone by interdigitating into the bone trabeculae. Cementing a plastic or metal implant securely to natural bone has greatly improved the status of joint replacement over the prior state of merely implanting the component into the bone and hoping that it actually stayed securely in place. Cement fixation generally provides excellent short term results. However, younger, heavier, or more active individuals may find that the bond between cement and bone eventually breaks down. Consequently, a loosening or separation between the bone and the implant occurs.

To address the problem of cement breakage or implant separation, an alternative is to coat a surface of the implant with a porous material which allows the patient's bone to grow into the pores, thereby mechanically fixing the implant to bone or alternatively coating the implant with a calcium-phosphate type of ceramic which may chemically bond the implant to bone. As a result in either case, the implant is biologically attached to the bone. This "cementless" procedure represents the current state of the art in implantation of joint prostheses. The patient's own tissue eventually holds the implant securely in place, either mechanically or chemically, and the implant subsequently becomes a permanent part of the bone.

Another problem, seen with both cemented and cementless implants, is occasional extensive osteolysis. This osteolysis, or bone dissolution, occurs throughout all areas of the bone into which the stem was implanted. The etiology is possibly a histiocytic foreign body reaction. In the case of cemented devices, the reaction may be from fractured particulate cement and/or secondary to polyethylene particulate wear debris. In the case of cementless stemmed implants, the reaction is felt to be secondary to particulate polyethylene or particulate metal alloy from fretting wear of the implant. Regarding reaction to metal alloy, fretting secondary to micromotion at the implant-bone interface theoretically initiates the foreign body immune response.

A further problem encountered with joint implants is an abnormal stress transference from the implant to the bone. The ideal stress transference of load to the bone is the normal, anatomical transference. To approximate it, the implant material should have mechanical properties similar to those of bone and should replace only the destroyed joint surface. Thus no implant material, or only a minimal amount of implant material, would be placed in the intramedullary canal of the bone. This is difficult to do with implants having porous surfaces. The reason is that such implants require immediate rigid fixation for a sufficient time period, at least six to twelve weeks, to assure bony attachment or chemical bonding. If the device is not held rigidly, micro-motion occurs at the implant-bone interface. The result is a less stable fibrous tissue interface rather than the necessary, more stable, securely-fixed bony attachment.

Currently the most common method of holding the implant rigidly in the bone is by providing the implant with a stem. The stem "press-fits" into the intramedullary cavity of the bone, e.g., the femur. Such a press-fit of the stem into the shaft of the bone holds the device rigidly and allows for an adequate bone attachment or chemical bonding for secure fixation. For the surgeon it also provides the desired proper anatomical placement of the implant in the bone in a reproducible manner. If no intramedullary cavity is available, as in the pelvis for example, the implant is anchored to the bone with a threaded anchor bolt.

The shortcoming of the aforesaid approach is that loading of the bone is no longer physiologic. Instead of the normal loading primarily at the end of the bone near the joint surface, the bone is loaded more distally where the stem of the implant is affixed. The result is an abnormal transference of stress which bypasses or "unloads" the end or joint surface portion of the bone. Consequently that portion of bone undergoes resorption. This leads to weakening over a period of years, thus creating a potential for fracture or resorption of the bone that previously held the implant securely. The result is again a loosening of the implant within the bone with all the adverse consequences previously mentioned.

For implants which are held in place with a screw, such as an acetabular cup of a hip prosthesis, the non-physiologic transference of stresses is less pronounced. This is because the location and orientation of the anchoring bolt can be selected to minimize non-natural load transference stresses. Nevertheless, the potential problems remain; namely, fretting with resultant corrosion and lysis or fatigue failure from micro-motion and eventual fracture of the anchoring bolt.

Because a stem placed down the medullary cavity of the bone produces an abnormal stress distribution, the possibility of using an implant without a stem presents itself. Such an implant would essentially only resurface the destroyed articular surface. This is more readily done in certain joints, such as the knee, elbow, or ankle, than in others, such as the hip, shoulder or wrist.

However, even if a stemless implant is feasible, its immediate rigid fixation is not as secure as if the implant were anchored with a stem or a bolt. Because the stem or bolt functions to align an implant in its correct position until bone attachment is complete, an alternative mechanism is necessary to accomplish these functions if a stemless implant is used. One such mechanism could be transcortical fixation of the implant with multiple screws. This, however, makes it more difficult for the surgeon to correctly and reproducibly position and align the implant. An alternative approach is disclosed and claimed in U.S. Pat. No. 4,990,161 the entire disclosure of which is made part hereof and incorporated herein by reference.

SUMMARY OF THE INVENTION

To approximate an ideal physiologic stress transference across a bone joint, the implant stem or anchor should fit tightly into place with respect to the natural bone. The implant may be porous-coated as well as coated with a chemical material such as calcium-phosphate ceramics to permit bony attachment and/or chemical bonding therein. Finally, the implant should not interfere substantially with stress transference in the long term. One approach to provide these features is found U.S. Pat. No. 4,990,161, the disclosure of which is incorporated herein by reference.

The '161 patent provides an implant with an anchor comprised of a biodegradable material. The biodegradable anchor includes an elongated member which has an exterior surface shaped to tightly engage a bone cavity. Because of the tight engagement, the anchor is substantially immovable within the cavity upon implantation. The anchor is made of a material which resorbs at preselected time periods after implantation, such as a number of weeks or months up to approximately one year or more.

Unfortunately, totally resorbable polymers do not necessarily possess the structural strength and integrity for a load-bearing stem. To overcome this problem and provide the required strength and rigidity, an implant constructed in accordance with the present invention has a composite anchor, including a stem having a nonresorbable core surrounded by a layer of resorbable material. The core increases the mechanical strength required for a load bearing anchor, such as in the hip or knee. For long bone or joint implants, the core extends from the permanent articulating bearing surface component into the medullary canal.

Initially, the resorbable layer gives secure anchorage of the stem with an interference fit equivalent to that obtainable with the current state of the art in prosthetic joint replacement. Selected surface portions of the permanent implant component are porous to permit and direct bony attachment. A coating of calcium phosphate may be provided to enhance bony ingrowth and possibly chemically bond the implant to bone.

After an optimal period of time elapses to permit sufficient bony attachment around the permanent, porous implant component, the polymer surrounding the metal core of the anchor slowly degrades and ultimately disappears. As a result, only the small diameter nonresorbable core remains in the medullary cavity of the bone. Although a small diameter core remains permanently within the medullary canal, no load bearing occurs through that core because it is spaced apart from cortical bone and, therefore, does not come in contact with the surrounding cortical bone structure. The core becomes essentially nonfunctional and the bone does not "realize" that any stem is actually present. In biomechanical terms only the permanent implant component forming the articulating surface of the joint remains as a permanent functional component and it is the only artificial component across which stresses are being transferred.

Thus, the present invention provides an implant with an anchor including a nonresorbable core surrounded by a resorbable sleeve. The nonresorbable core strengthens and reinforces the sleeve. The core is sized so that it can not accept significant load bearing. Consequently, once the sleeve is resorbed, the nonresorbable core is nonfunctional and does not impede normal stress transfer.

The invention negates the problem of distal loading of the bone with resultant proximal bone resorption seen with stemmed devices. Problems such as those seen in hip replacement arthroplasty are eliminated or minimized. Because the remaining small diameter core is essentially free floating within the medullary cavity, fretting with potential for osteolysis is no longer a significant potential.

Selected portions of the implant surface intended to contact the bone are porous. Such a surface promotes bony attachment to further anchor the implant and to approximate the natural mode and stress transference situation after bony ingrowth has occurred. After the stem is no longer required, the resorbable sleeve disappears by a natural biologic erosion. The resorption of the sleeve material can be predetermined to take place over any desired length of time, i.e, six weeks, eight weeks, twelve weeks, six months, one year or more. These factors will depend on how much time the particular bone normally takes to adequately attach to the implant as well as clinical considerations such as the age and overall health and mobility of the individual.

The nonresorbable core is typically formed from a metal alloy such as a titanium alloy, most preferably titanium-6-aluminum-4-vanadium. Alternatively, other alloys of cobalt-chromium or stainless steel may be employed. Other materials which can be used for the core include nonresorbable ceramics such as aluminum oxide and zirconia. The permanent implant can also be formed from materials such as nonresorbable plastics, e.g., polyethylene or even composite materials such as carbon fiber-reinforced polymers such as polysulfone.

Generally, articulating surfaces of the permanent, functional implant are formed of permanent nonresorbable materials such as a metal alloy, ceramic, carbon and polymers. Preferred alloys are titanium, such as titanium-6-aluminum-4-vanadium. Other alloys include cobalt-chromium and stainless steel. Ceramics suitable for permanent articulating surfaces include aluminum oxide and zirconia.

The length and diameter of the elongated, composite anchor or stem will vary according to the physical characteristics of the patient. Preferably, diameter variations are achieved by varying the thickness of the resorbable sleeve.

Modular construction is most preferred where practical to facilitate interchange of parts and thereby minimize the inventory of parts that must be kept. For example, a head or ball component of a hip replacement is preferably of modular construction to cooperate with a neck portion. Also, stem or anchor portions having an inner permanent core and an outer resorbable sleeve are preferably formed by modular construction. Taper locks are preferably used for interconnecting the parts which make up a complete implant.

The resorbable sleeve and resorbable anchoring bolts or screws are fabricated from a variety of biodegradable materials. Many examples of such materials are known to the artisan, including certain ceramics such as calcium hydroxyapatite or tricalcium phosphate, high molecular weight poly-L-lactic acid (PLLA) polymers, such as that used to fabricate currently used bioresorbable screws, adapted to prosthetic implants, other polymers, such as polymers of glycolic acid or lactic acid, polyamides of α-amino acids, polydioxanone, polylactic acid-polyglycolic acid copolymers, polyorthoester, polycarbonate and polyetheretherketone (PEEK). Also, unmodified or modified natural polymers such as gelatin or starch can be used.

BRIEF DESCRIPTION OF THE DRAWINGS

FIG. 4 is a schematic front elevation view of a prosthetic knee constructed in accordance with the present invention;

FIG. 7 is a cross-sectional view taken along line 7—7 of FIG. 3.

DESCRIPTION OF THE PREFERRED EMBODIMENT

Figure 1:
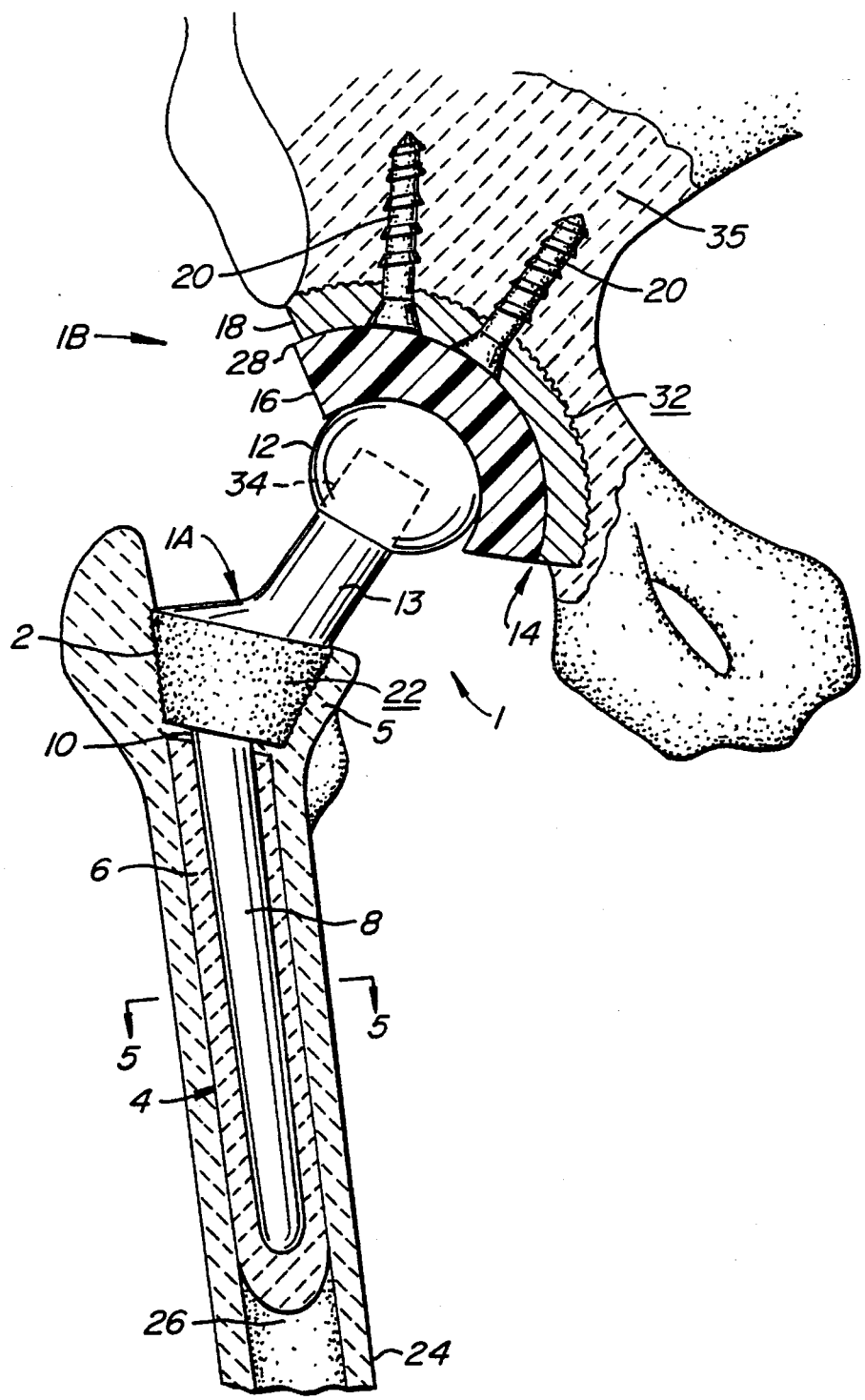
FIG. 1 is a schematic, front elevation view through a human hip joint, illustrating the pelvis and the upper portion of the femur, and shows a prosthetic hip constructed in accordance with the present invention immediately after installation.

Referring to FIG. 1, a total prosthetic hip constructed in accordance with the present invention is made up of a femoral implant 1A and an acetabular implant 1B. The femoral implant includes a trochanteric body piece 2 which has a porous surface 22 over the portion of its exterior which is intended to be directly affixed to the natural bone. To achieve the desired bony ingrowth, pores of the porous surface are preferably sized in a range between about 250–450 μ. The exact dimensioning of the pores is known to those skilled in the art and is not particularly critical. Also included is an anchor 4 which is comprised of a permanent core 8 and a resorbable sleeve 6. Core 8 is preferably made of a metal alloy such as titanium-6-aluminum-4-vanadium.

Outer resorbable sleeve 6 is formed of a biodegradable material, for example, high molecular weight poly-L-lactic acid (PLLA) polymers. Other such materials include calcium hydroxyapatite, tricalcium phosphate and the compounds previously mentioned.

In a preferred embodiment, anchor 4 is affixed to trochanteric body piece 2 by means of a taper lock 10. Preferably anchor 4 includes a female portion and trochanteric body piece 2 includes a male portion of taper lock 10. The male and female portions have cooperating surfaces which are tapered at an angle selected so that they become effectively permanently secured to each other when the two portions are firmly pushed together. The female portion is preferably formed in anchor 4 so as to prevent formation of stress concentrations in the trochanteric body piece 2. The interconnection between trochanteric body 2 and anchor 4 is typically in the region of anchor 4 which straightens out in a lateral plane, although it may be located at other sites along anchor 4.

This modular construction of the femoral implant 1A makes it possible to stock an inventory of differently shaped and/or sized components that can be assembled to fit any given patient. Thus, resorbable outer sleeve 6 has multiple outer diameter sizes to fit different medullary shaft diameters while inner core 8 has a constant diameter so that the outer diameter of anchor 4 varies with the thickness of resorbable sleeve 6. In addition, the parts inventory will include anchors of varying lengths. Thus, the surgeon can select the permanent implant and the anchor which have the desired dimensions and shapes from the available inventory, assemble them with the above-discussed taper locks, and then install the implant in the patient.

In another embodiment the cross section of inner core 8 of anchor 4 is not rounded, but, for example, a quadrilateral, e.g., square or rectangular. See FIG. 4. By extending the square cross section to taper lock 10 it is possible to predetermine the relative angular orientation of the modular components of the implant. Anchor 4 is inserted by press fitting into place.

Trochanteric body piece 2 is in continuity with a modular head or ball 12, preferably formed of metal alloy such as a titanium alloy. Titanium-6-aluminum-4-vanadium is a preferred alloy. Other suitable alloys include cobalt-chromium and stainless steel. Trochanteric body piece 2 is connected to head 12 by a neck 13 which extends medially and upwardly with respect to trochanteric body piece 2. Head 12 cooperates with an acetabular cup 14 of the acetabular implant 1A.

In one embodiment, neck 13 forms a taper lock 34 with head 12 to secure the two to each other. Head 12 preferably has a female aperture which cooperates with a male extension of neck 13 to form the taper lock 34. Alternatively, other locking means, such as a threaded screw arrangement (not separately illustrated), can be used.

The acetabular implant includes an inner acetabular component 16 and an outer acetabular component 18. Inner component 16 is preferably formed of polyethylene although other noncorroding, nonresorbable high strength materials can be used. Outer acetabular component 18 is formed of titanium alloy although other high-strength materials, such as cobalt chromium alloy, stainless steel alloy and ceramics, can be used. The femoral head is preferably formed of zirconia.

Inner acetabular component 16 is cup-shaped and has a concave surface facing and engaging ball 12 of the femoral implant and permitting free movement of the ball in the socket. Outer acetabular component 18 includes multiple fixation holes, or alternatively a single bore, positioned so that upon implantation the bore is aligned with a pectineal line of the patient's pelvis as is described in greater detail in U.S. Pat. No. 4,990,161.

Preferably, resorbable screws 20 are used to secure acetabular cup 14 to pelvic bone 35. Alternatively, the holes and bore can include a recess defining an inwardly facing shoulder that, upon implantation, engages a set screw having a threaded end extending into and engaging screw 20 (as is more fully described in U.S. Pat. No. 4,990,161). The set screw is nonresorbable and acts as an interconnection between resorbable screw 20 and nonresorbable outer component 18.

The exterior surface of outer component 18 in contact with the bone of the patient's pelvis and where stress transference is to take place has a porous surface 32 for anchorage of component to bone. Porous surface 32 promotes bone ingrowth into the area of load transfer between the pelvis and acetabular cup 14. To achieve the desired ingrowth, the pores are preferably sized in a range between about 250–450 μ.

Inner and outer acetabular components 16/18 are held together by means known to the artisan. Typically, a lip is provided on one of components 16/18 and a key arrangement locks components 16/18 together.

Resorbable screw 20 has a first end including an external thread formed to cut into and firmly engage the bone structure. Resorbable screws 20 are typically 6.5 mm in diameter. In a presently less preferred alternative, an opposite free end of screw 20 includes an internal thread which is engaged by a nonresorbable set screw.

Screw 20 is preferably fabricated from a resorbable material such as modified or unmodified natural polymers, biodegradable ceramics, and other materials known to the artisan. The material is engineered to resorb at a predetermined time. For most applications, this time will coincide with a time period sufficient to allow mature bony attachment about acetabular component 14 for adequate mechanical fixation of the implant to the pelvis.

During implantation, resorbable screw 20 is aligned with the bone of the natural acetabular cup. Screw 20 is tightened to firmly secure acetabular cup 14 to the bone. After implantation, inner component 16 may be positioned so that an overhanging portion 28 protrudes beyond the natural cup. This provides better seating of ball or head 12 over a wider range of motion and helps prevent accidental dislocations of ball or head 12 and the socket.

To implant the femoral implant 1A into a femur 24, the head and neck of femur 24 are resected and an external femoral loading face is formed. The loading face is planar and generally perpendicular to a pectineal line and at an angle of approximately 70° to a longitudinal axis of femur 24. A cavity is shaped in the intertrochanteric aspect of the femur 5 by removing soft non-load bearing bone tissue which is mostly marrow. The entire intertrochanteric cavity may be broached slightly under size relative to the implant to achieve a secure press fit.

Trochanteric body 2 has a nonresorbable male taper lock depending therefrom. Prior to implantation, anchor 4 is connected to trochanteric body 2 by pressing a portion of taper lock 10 of body 2 into a reciprocating portion of taper lock 10 formed in anchor 4. Alternatively, this lock can be a screw connection.

Trochanteric body 2, including anchor 4, is pressed into the appropriately dimensioned intertrochanteric upwardly opening cavity in femur 24 until the internal and external loading surfaces firmly engage the bone. During the implantation process, elongated anchor 4 slides into the medullary canal of the femur and acts as a guide to prevent misalignment of trochanteric body 2 during the insertion. This is particularly important when substantial force must be applied to overcome the press fit between the body and the cavity.

Resorbable sleeve 6 firmly engages the walls of the medullary canal with a press fit to secure and fix anchor 4 and trochanteric body 2 until bony ingrowth has attached body 2 to the patient's own femur. Inner metallic core 8 acts as a reinforcement to strengthen anchor 4 and prevent it from cracking, breaking or otherwise deforming. After sleeve 6 is totally resorbed, inner core 8 is essentially free floating within, that is, it does not contact the cortical walls of, medullary cavity 26 and it is sized such that it does not accept loads.

Once the implant is firmly fixed by bony attachment in its proper position, the function of anchor 4 is over and its functional portion, sleeve 6, is eliminated by resorption. The final result is a functionally stemless femoral component that allows a near perfect physiologic transference of stresses to the proximal femur as opposed to a stemmed implant which is fixed distally. Distal fixation, as encountered with permanent stems which remain in contact with cortical bone, creates a potential for stress shielding and bone resorption proximally with an increased chance of mechanical failure.

After implantation, after proximal bony attachment and after resorption of outer sleeve 6, there is no significant distal loading on the bone. This is the normal physiologic and anatomic situation. The absence of such distal loading about the femoral cortex adjacent to anchor 4 coupled with the transfer of loading and stresses proximally assures that the femoral implant is top loaded in a manner analogous to the normal femur in a healthy hip joint.

Figure 2:
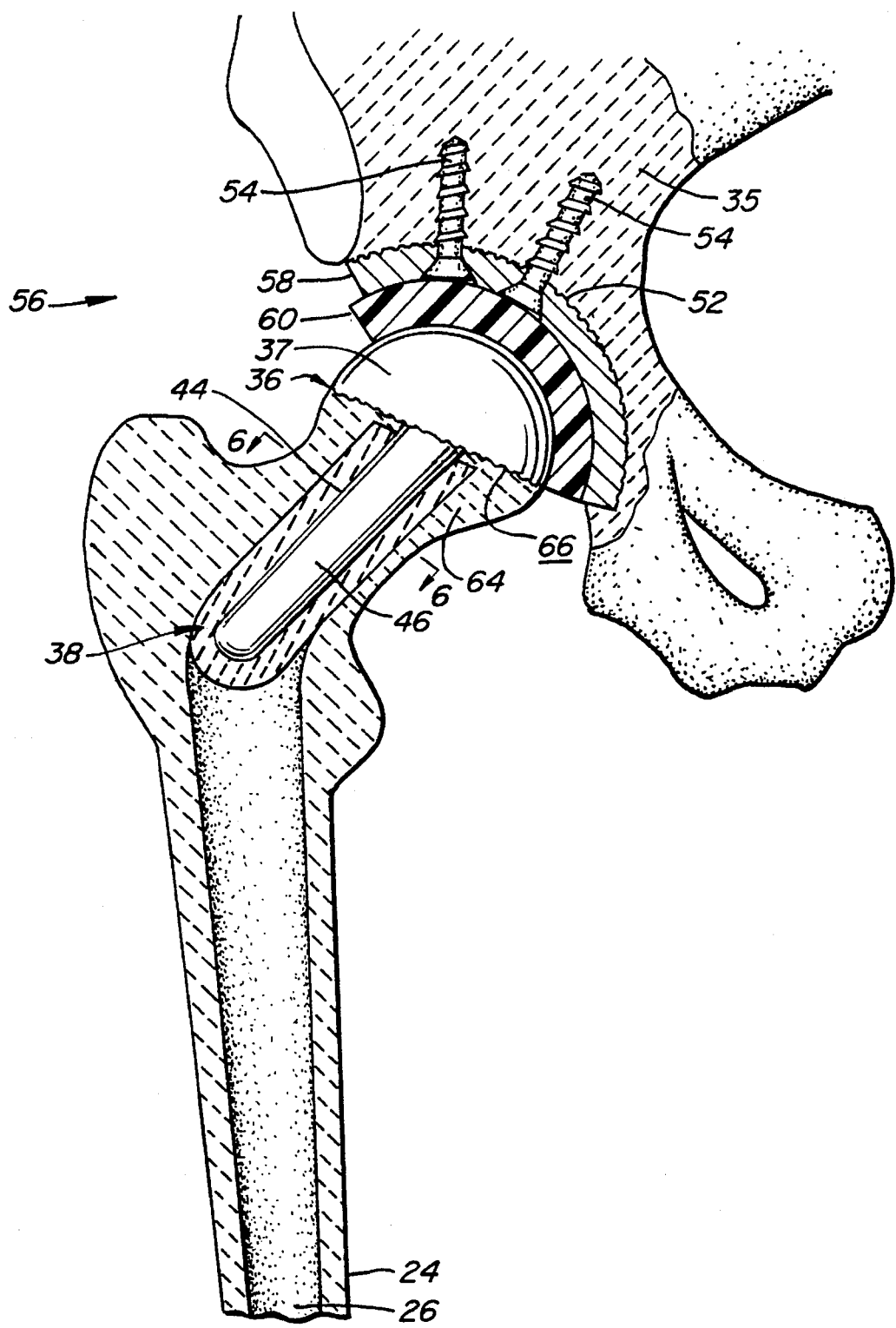
FIG. 2 is a schematic front elevation view through a human hip joint illustrating an alternate embodiment of a prosthetic hip constructed in accordance with the present invention.

FIG. 2 illustrates an alternative embodiment of the femoral implant of the present invention. It comprises a resurface femoral head implant 36 having an anchor 38. Anchor 38 includes a resorbable sleeve 44 surrounding a nonresorbable inner core 46. Resurface component 36 is formed of a nonresorbable material, preferably a metal alloy. Implant 36 defines a generally semi-spherical head 37 which is shaped to fit into and cooperate with an acetabular cup 56 upon implantation. The surgeon selects implant 36 from an inventory of several, perhaps 4 or 5, sizes varying from small to large.

Resurface component 36 is placed in contact with a patient's transected femoral head 64. This transection across the femoral head should be inclined approximately 70° to the longitudinal axis of the femur so that the applied loading forces act substantially perpendicular to the implant surface. Consequently, substantially only compressive forces are generated between the implant and the femur with theoretical enhancement and earlier bony attachment over the exterior load transferring implant surface. This 70° inclination being perpendicular to the implant surface would tend to enhance stabilization of the implant following resorption of the resorbable sleeve. Resurface implant 36 protrudes from the generally planar surface of a partially resected femoral head 64. A porous surface 66 is defined by a portion of the implant which is in intimate contact with the transected femur head 64. Porous surface 66 promotes bony attachment of the implant to the femur.

Figure 3:
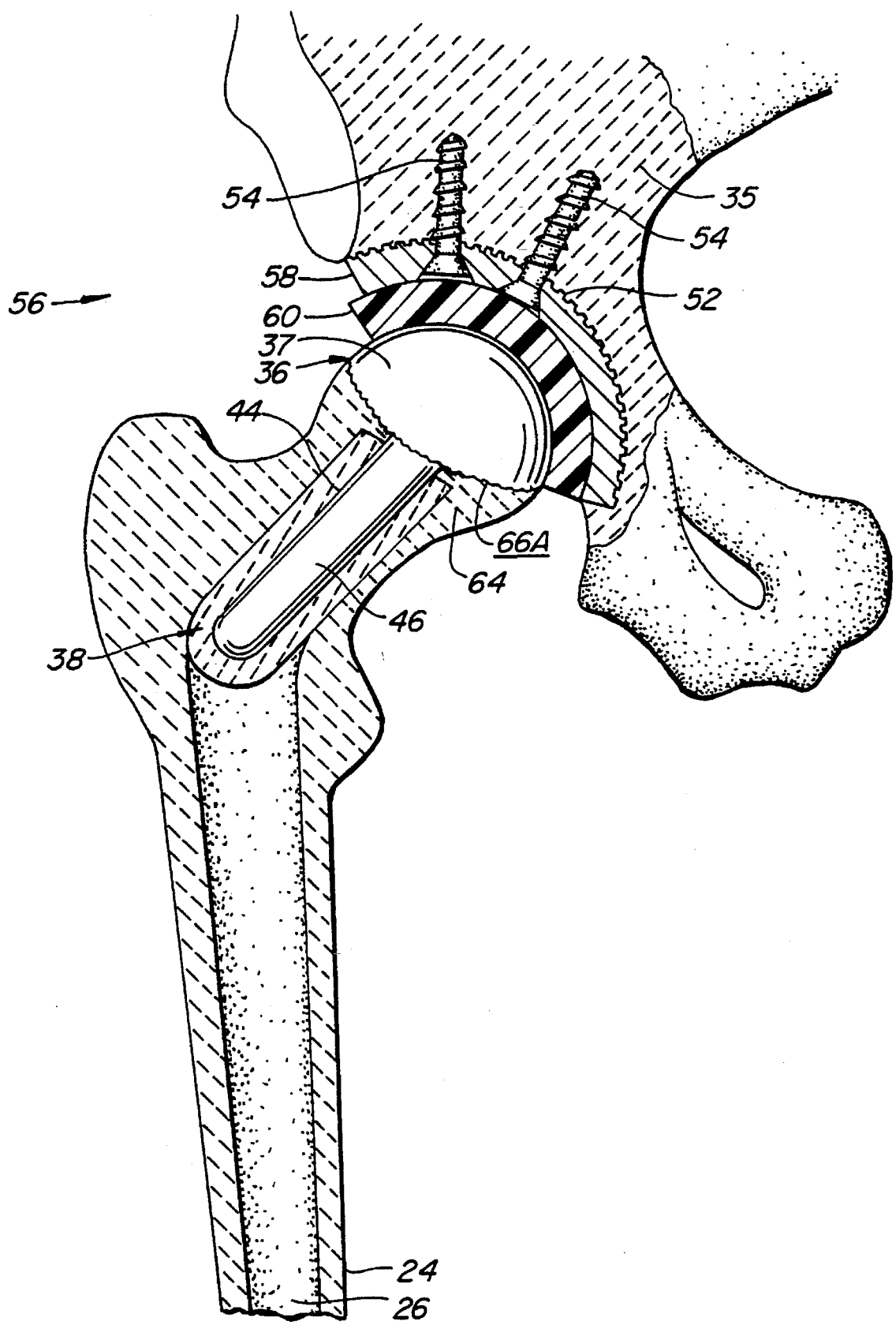
FIG. 3 is a schematic front elevation view through a human hip joint illustrating a further embodiment of a resurface femoral head component making the 70° inclination concave rather than planar.

FIG. 3 is an illustration of a further embodiment of a resurface femoral head component making the 70° inclination concave rather than planar, thus affording greater stability of the implant. Thus, surface 66a is curved instead of being substantially planar.

Core 46 is preferably formed as one piece with head 37. Alternatively, core 36 can be secured to resurface component 36 by any number of means known in the art, e.g., with the above-described taper lock or with a threaded connection. Anchor 38 extends in a lateral and downward direction with respect to head 37. That is, a lower or distal surface of implant 36 which contacts partially resected femoral head 64 is placed at approximately a 70° cut angle with a longitudinal axis of femur 24.

Figure 5:
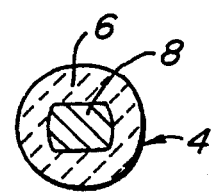
FIG. 5 is a cross-sectional view taken along line 5—5 of FIG. 1.

Anchor 38 is seated tightly into intramedullary canal 26 with a press-fit. Resorbable sleeve 44 may be tapered and dimensioned to interface the breached bone canal. A cross-sectional view of either anchor 38 shows a quadrilateral inner core cross section., most preferably of a square or rectangular shape. See FIG. 5.

Anchor 38 is preferably also of modular construction as described above so that the size appropriate for a given patient can be selected from an inventory of differently sized and/or shaped anchors. The modules are connected just prior to implantation with a taper lock, for example. For optimal efficiency, the inventory consists of a select number of cores 46 of equal diameter but differing lengths and a number of resorbable sleeves 44, all having the same inner diameter so that they fit snugly onto any of the cores but of different outer diameter so that they can be press-fit into medullary canals of varying diameters. The optimal length of the combined core and sleeve would be such that it would contact the lateral cortical wall of the femur distal to the greater trochanter and opposite the lesser trochanter thus further stabilizing the implant.

Finally, the sleeves will have a sufficient length so that they can be fitted onto the largest core. For shorter cores, the sleeve is cut to the appropriate length just prior to assembly and installation.

Acetabular cup 56 is constructed as described above and includes an outer component 58 and an inner component 60. The outer component is usually formed of a metal alloy, such as a titanium alloy. Inner component 60 is preferably formed of polyethylene. Other materials are suitable as discussed above. The outer component 58 is provided with a porous surface 52 as well as possibly being coated with calcium phosphate to direct and encourage bony attachment as previously discussed.

Outer and inner components 58/60 are held together by means known in the art as discussed above. Resorbable screws 54 hold outer component 58 to pelvic bone 35 until bony attachment occurs. Resorbable screws 54 are typically 6.5 mm in diameter.

Figure 6:
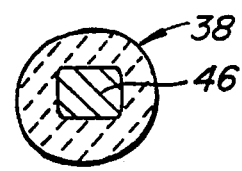
FIG. 6 is a cross-sectional view taken along line 6—6 of FIG. 2.

Turning now to FIG. 4, a total knee prosthesis constructed in accordance with the present invention is shown. The prosthesis includes a femoral component 70 and a tibial component 90. Femoral component 70 includes a stem 74 having a resorbable outer sleeve 76 and an inner nonresorbable core 78. Inner core 78 is typically formed of a metal alloy such as a titanium alloy, preferably titanium-6-aluminum-4-vanadium. The stem can be of a modular construction as previously described. A cross-sectional view of stem 74 shows a quadrilateral-shaped core dimension as previously discussed. See FIG. 6.

Femoral component 70 also includes an articular bearing surface which is preferably formed of a metal alloy. A selected portion of articular bearing component 72 to be in contact with the natural femur has a porous surface 84 for bony attachment. Articular bearing component 72 terminates proximally in a portion of a lock, preferably a taper lock 80. Alternatively a screw-type lock may be utilized.

The portion of taper lock 80 of femoral component 72 is preferably a female portion. Taper lock 80 is designed to cooperate with a distal termination of stem 74 which includes an opposite cooperating portion of lock 80, preferably a male portion of taper lock 80.

Tibial component 90 includes a stem 92 which is comprised of an inner nonresorbable core 96 and a resorbable outer sleeve 94. Inner core 96 is formed of a metal alloy. A preferred alloy is titanium-6-aluminum-4-vanadium although other alloys, such as cobalt-chromium or stainless steel, can be used. Resorbable outer sleeve 94 is again preferably of modular construction as is inner metal core 96. Inner metal core 96 preferably has a cross-section which is quadrilateral in shape, preferably square or rectangular, to reduce possible slippage or torsion.

Inner metal core 96 terminates proximally in a portion of a taper lock 98, preferably a male portion which cooperates with a female termination of a tibial tray component 88. Tibial tray 88 is nonresorbable and is preferably formed of a metal alloy such as titanium-6-aluminum-4-vanadium. At a lower or distal surface of tibial tray 88, there is a porous surface 82 for the desired bony attachment.

Proximal to tibial tray 88 is a bearing component 86 which can be made of polyethylene, ceramic or even a metal alloy. Bearing component 86 is in contact at its lower or distal surface with an upper or proximal surface of tibial tray 88.

Bearing component 86 and tibial tray 88 are held together by means well known to the artisan. Usually, one of tibial tray 88 or bearing component 86 is provided with a lip. A key arrangement locks the two components together. Resorbable screws 100 anchor tibial tray 88 to the patient's tibia until bony attachment into the lower surface of tibial tray 88 assures bony fixation.

Bearing component 86 is configured at its upper or proximal surface with two cup-shaped or concave portions designed to cooperate with femoral component 72. Femoral component 72 is provided at its lower or distal surface with projections which are convex and cooperating to adapt with the configuration of bearing component 86. This arrangement is in imitation of the natural human knee joint. That is, the femoral projections of femoral component 72 represent and mimic the femoral condyles and the upper or proximal surface of bearing component 86 is shaped to mimic the articulating surface of the proximal tibia.

In installation, femoral implant 70 is inserted into the patient's femoral medullary cavity after resection of the distal femur. Resected portions include the articulating surfaces. Femoral implant 70 is inserted after opening of a cavity in the femoral shaft. Femoral stem component 70 acts as an alignment and anchoring mechanism for the artificial joint.

In similar fashion, an appropriately dimensioned area in the tibial medullary shaft is opened. After appropriate resection of the proximal tibial area including the articulating surface, tibial component 90 is placed into the opening in the patient's tibial medullary shaft. Tibial stem component 90 acts as an alignment and anchoring mechanism for the artificial knee joint.

Femoral articular bearing component 72 has a porous surface 84 which is in intimate contact with the transected natural femur. Similarly, the porous surface 82 of tibial tray component 88 is in intimate contact with the transected natural tibia. Porous surfaces 84/82 permit and direct bony ingrowth into the prosthetic devices to permanently anchor them. After bony attachment has occurred, the resorbable materials, including sleeve 76 of femoral implant 70 and sleeve 94 of tibial implant 90, resorb over a predetermined time period.

After resorption of sleeves 76/94, remaining inner cores 78/96 are nonfunctional. That is, they are dimensioned such that they do not contact the bony cortices, thereby accepting no load bearing. Thus, the cores are essentially free floating within the medullary canal. As a consequence, no significant abnormal stress transference occurs, in contrast to conventional, non-resorbing stemmed devices.

Although hip and knee replacement have been described with particularity, the present invention is not so limited. Resorbable anchoring devices including a resorbable sleeve reinforced by an inner nonresorbable strengthening core are applicable to all joints including wrist, finger, elbow, ankle, foot, toe and shoulder. The artisan may readily appreciate other uses and variations of the present invention. The invention is not to be limited by the aforementioned examples but rather by the scope of the claims which follow.

What is claimed is:

1. An anchor for a bone joint implant adapted to be inserted in a cavity defined by a bone and having a given cross section for affixing the implant to the bone without substantial motion of the implant relative to the bone after affixation, the anchor comprising:

a nonresorbable core sized for insertion in the cavity and having a cross section sufficiently smaller than the cross section of the cavity so that contact between the bone and the core is prevented; and a resorbable sleeve applied to the core and having a size so that it tightly engages the cavity in the bone to thereby immovably secure the anchor to the bone.

2. The anchor of claim 1 further comprising:

a permanent, articulating implant component having a surface to contact the bone and a surface to interact with a cooperating surface of a joint; and a securing means for joining the articulating implant component to the core.

3. The anchor of claim 2 wherein the securing means comprises a taper lock.

4. The anchor of claim 1 wherein the core is formed of a metal alloy selected from a group consisting of titanium-6-aluminum-4-vanadium, cobalt-chromium, and stainless steel.

5. The anchor of claim 1 wherein the resorbable sleeve is formed from a material selected from a group consisting of polymers of glycolic acid, polymers of lactic acid, polyamides of α-amino acids, polyglycolic acid, polylactic acid-polyglycolic acid copolymers, polyetheretherketone (PEEK), polyorthoester, polycarbonate, calcium hydroxyapatite and tricalcium phosphate.

6. The anchor of claim 1 wherein the anchor is part of a prosthetic hip.

7. An implant for a bone joint comprising:

a component defining an operative portion of the joint, the component having an interface facing generally away from the joint and adapted to be placed into intimate contact with an actual bone to which the component is to be fixed, at least part of the interface including means promoting bony ingrowth when the interface is in intimate contact with the natural bone; and an anchor connected to the component and adapted to be inserted in a cavity in the bone for orienting and immovably fixing the component to the bone immediately upon implantation, the anchor comprising:

a relatively high strength, permanent core having a cross section sufficiently smaller than the cross section of the cavity so that contact between the bone and the core is prevented;

an outer layer applied to the core and shaped so that the layer, upon implantation, securely engages a bone surface defining the cavity, the layer being constructed of biodegradable material so that it resorbs after a period of time and thereby vacates a portion of the cavity; and whereby, after the layer has resorbed, the core of the anchor is spaced from and out of contact with the bone surface defining the cavity so that substantially no load transference between the bone surface defining the cavity and the core takes place.

8. The implant of claim 7 further comprising means for removably securing the anchor to the component.

9. The implant of claim 8 wherein the securing means comprises a taper lock defined by the component and the core.

10. The implant of claim 7 wherein the component comprises a joint socket.

11. The implant of claim 7 wherein the component comprises a convex surface adapted to cooperate with a concave surface of another joint member.

12. The implant of claim 11 wherein the convex surface is defined by a ball joint member.

13. The implant of claim 12 wherein the component further includes a body connected with the ball and defining the interface.

14. The implant of claim 13 including means for detachably securing the body and the ball to each other.

15. The implant of claim 7 wherein the outer layer is removably connected to the core to enable the selection of the outer layer from a supply of differently formed outer layers and thereby fit the outer layer to the shape of the cavity.

16. An implant for a bone joint comprising:

a component defining an operative portion of the joint, the component including a ball joint member, a body having an interface facing generally away from the joint and adapted to be placed into intimate contact with an actual bone to which the component is to be fixed, at least part of the interface including means promoting bony ingrowth when the interface is in intimate contact with the natural bone and means for detachably securing the ball joint member and the body to each other; and an anchor connected to the component and adapted to be inserted in a cavity in the bone for orienting and immovably fixing the component to the bone immediately upon implantation, the anchor comprising:

a relatively high strength, permanent core having a cross section sufficiently smaller than the cross section of the cavity so that contact between the bone and the core is prevented;

an outer layer applied to the core and shaped so that the layer, upon implantation, securely engages a bone surface defining the cavity, the layer being constructed of biodegradable material so that it resorbs after a period of time and thereby vacates a portion of the cavity; and whereby, after the layer has resorbed, the core of the anchor is spaced from and out of contact with the bone surface defining the cavity so that substantially no load transference between the bone surface defining the cavity and the core takes place.

* * * * *